(12) United States Patent
Giordano

(10) Patent No.: US 6,188,929 B1
(45) Date of Patent: Feb. 13, 2001

(54) SEQUENTIALLY GENERATED MULTI-PARAMETER BIO-ELECTRIC DELIVERY SYSTEM AND METHOD

(76) Inventor: Joseph Giordano, 2436 Legacy Island Cir., Henderson, NV (US) 89014

( * ) Notice: Under 35 U.S.C. 154(b), the term of this patent shall be extended for 0 days.

(21) Appl. No.: 09/354,283

(22) Filed: Jul. 15, 1999

(51) Int. Cl.[7] .................................................. A61N 1/08
(52) U.S. Cl. ................................................... 607/59
(58) Field of Search ........................ 607/59, 2, 46, 607/48, 50, 62, 96

(56) References Cited

U.S. PATENT DOCUMENTS

| 4,338,945 | 7/1982 | Kosugi . |
|---|---|---|
| 4,431,000 | 2/1984 | Butler . |
| 4,541,432 | 9/1985 | Molina-Negro . |
| 4,571,556 | 2/1986 | Gnerlich . |
| 4,598,713 | 7/1986 | Hansjuregens . |
| 5,573,552 | 11/1996 | Hansjurgens . |

*Primary Examiner*—Kennedy Schaetzle
(74) *Attorney, Agent, or Firm*—Philip J. Anderson; Anderson & Morishita, LLC

(57) ABSTRACT

A device and method are set forth for electro-stimulation. The user can select an overall treatment protocol of current frequencies and amplitudes to be applied for specified dwell periods defining a sweep cycle. The user can select for one or more periods in the cycle a frequency/amplitude to be applied to elicit a response such as a muscle contraction or the like. The device protocols may be selected to elicit responses while conserving power, to provide for heating without eliciting a response or to hop between frequency/amplitude combinations to produce the desired effect.

21 Claims, 7 Drawing Sheets

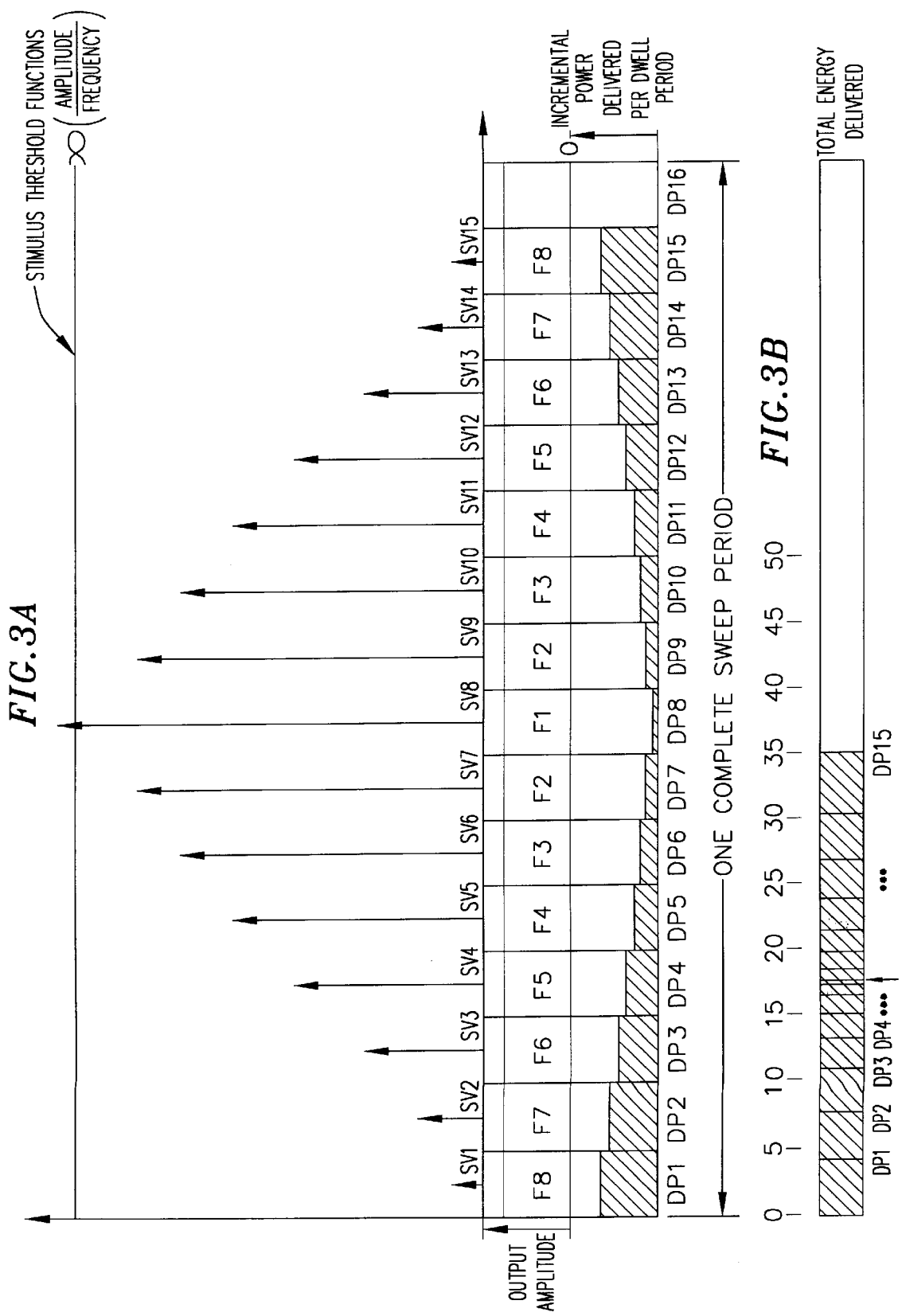

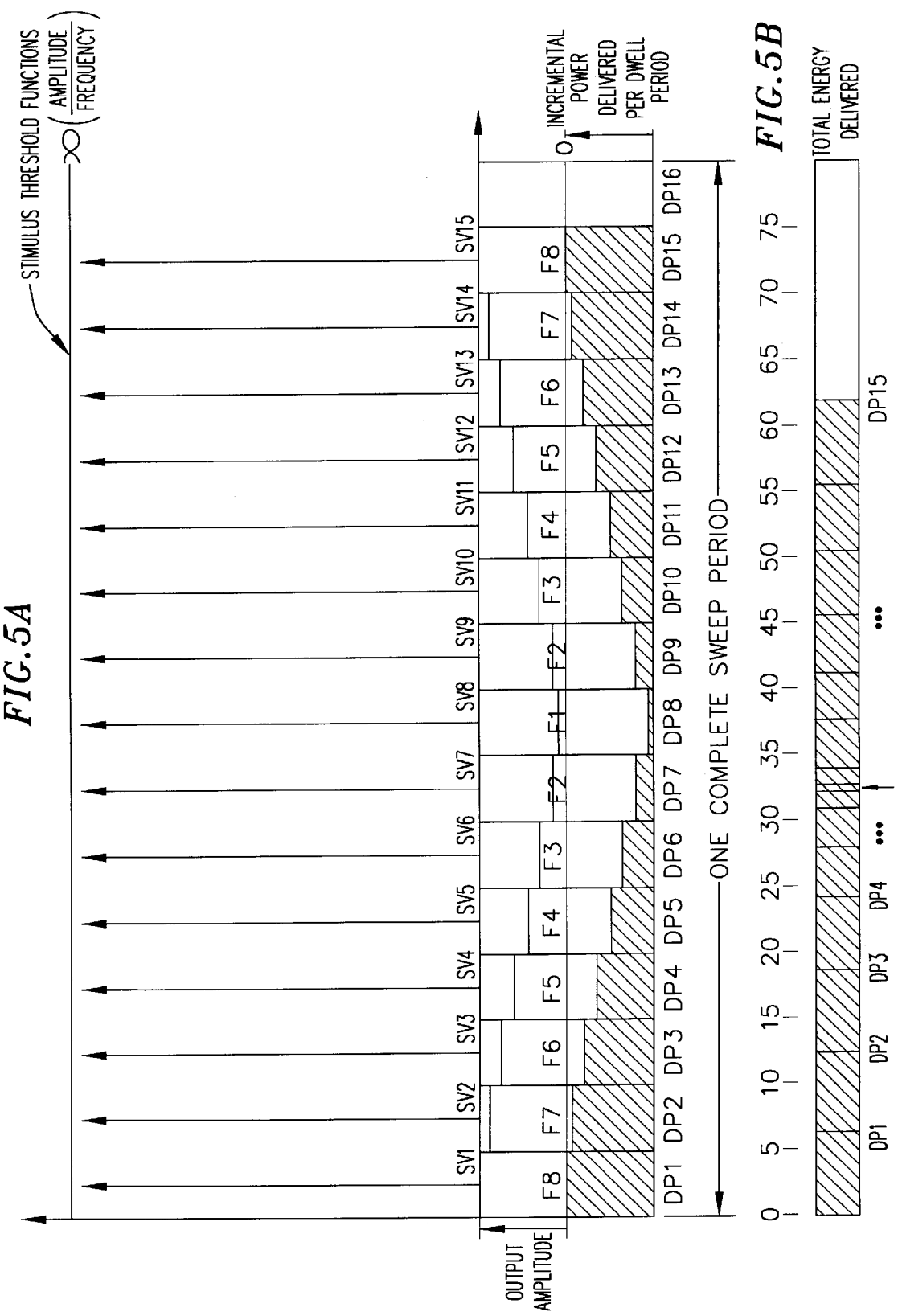

SEQUENTIALLY GENERATED MULTI-PARAMETER BIO-ELECTRIC DELIVERY SYSTEM AND METHOD

FIELD OF THE INVENTION

The present invention relates, to device for providing electrical stimulation to tissue, muscles, bones and nerves for producing a therapeutic effect.

BACKGROUND OF THE INVENTION

Electrical devices and methods are known for providing electric stimulation to tissue and cells for desired therapeutic effects such as the type described in Hansjurgens, U.S. Pat. No. 5,573,552 the disclosure of which is hereby incorporated by reference. Generally these prior devices and methods are adapted to stimulate tissue and bone cells to promote healing and the like, to stimulate muscle contractions to provide a therapeutic effect thereto and to stimulate or block the transmission of signals by nerves to, for example, decrease or block pain. Also if heating is desired, the current applied to the tissue can be increased to induce heating of the cells also to produce a therapeutic effect or to destroy cells such as tumors or the like.

A drawback of the devices and methods suggested by Hansjurgens Pat. No. 5,573,552 (the '552 patent) is that their operation is premised upon using a constant amplitude while varying the frequency of the potential applied to the cell or nerve in a predetermined, ramping fashion. As described in the '552 patent, corner frequencies are selected, a lower comer frequency and a higher, upper corner frequency. These comer frequencies are selected to span the frequency (at the constant amplitude) which triggers the desired stimulus response (e.g. muscle contraction) in the tissue or nerve. Thus in most instances the upper corner frequency exceeds the frequency necessary to trigger the desired response. With a constant amplitude, the frequencies are modulated in a linear, ramping, sweeping, fashion between the lower and upper corner frequencies crossing, during their traversal up and down between these frequencies, exceeding the action potential frequency eliciting the stimulus response such as a muscle contraction which may be at, for example, 1500 Hz. It has been found that once a stimulus response has been elicited, that amplitude must be increased or frequency reduced to elicit another response. This phenomena is believed to be based upon the target such as a muscle, becomes conditioned not to respond to the same magnitude of stimulus. Thus the ramping approach described above has worked with a constant amplitude since frequency is varied during the ramping sweep of frequencies to trigger the stimulus response during the sweep and the upper corner frequencies have been selected to far exceed the value necessary to trigger the response. Thus even though the tissue becomes conditioned, the increasing values will ultimately elicit the response.

With reference to FIG. 1, there is shown the relationship between tissue impedance A, current delivered B, power C versus frequency. As can been seen the tissue impedance Z has an inverse relationship to frequency, i.e. decreases as frequency increases. Power P and current I have a direct, non-linear, relationship to frequency. For current I, if the voltage remains constant, the reduction in impedance Z with the increase in frequency, increases the current I delivered. Similarly, since power P is the product of voltage and current I, if voltage is held constant the power P will increase proportionately with the current I. Another relationship that is important to understand is that energy is the product of power and the length of time the power is delivered. FIG. 2 shows the relationship between energy and time for various frequencies. Line D represents, for example, a frequency of 20,000 Hz, line E for a frequency of 10,000 Hz, line F for a frequency of 5000 Hz and line G for a frequency of 2500 Hz.

Because the amplitude of the prior art system as described in the above patent is held constant (frequency is varied), there is no means to control the amount of energy (heat) which would be delivered without altering the lower and upper corner frequencies, i.e. starting points of the ramping sweep, or frequency step (the increase in frequency), frequency sequence or dwell time, i.e. how long the power is delivered at that frequency. Thus, one cannot alter one desired parameter such as energy without adjusting one or more of the other parameters. For example, one could not reduce the amount of energy delivered to consume less power, without, for example, lowering the corner frequencies and thus not, perhaps, obtaining the stimulus threshold required for stimulation of the tissue or nerve.

Furthermore these prior devices do not permit the operator to select a delivery protocol such as one to deliver multiple signals to elicit a stimulus response during a sweep cycle while minimizing the power required. Thus one could not heretofore select during a sweep period that a first stimulus response by induced during a first portion of the sweep, again near the middle of the sweep and again near the end of the sweep while the intervening intervals during the sweep are selected to minimize the power required.

There is a need for a device and method which overcomes the aforementioned drawbacks, which enables the selection of one or more events, such as a stimulation response, to occur during a sweep period and which otherwise selects parameters for the sweep corresponding to a desired, overall, protocol be it conservation of power, heating or the like.

SUMMARY OF THE INVENTION

There is, therefore, provided according to the present invention a multi-parameter bio-electric device for electro-stimulation which includes a data structure storing data at discrete addresses which corresponds to a current frequency and amplitude to be applied for a predetermined period of time, hereinafter referred to as a dwell period. Means are provided for selecting a therapy protocol to be delivered during a sweep cycle. One protocol may be to conserve power. Another may be to deliver heat. The selection means may be embodied as a computer processor at which the user may select between different protocols by using an input device such as a keyboard, switch, dial, mouse or other input device. Means are also provided for selecting at least one of the parameters of frequency and amplitude to be delivered during the sweep cycle. As but an example, the user may select frequencies and amplitudes to elicit two stimulation responses during a sweep period and may select the location and dwell period for the responses over the sweep cycle. A processor is programmed to, in response to the selection of the parameters and protocol to store at addresses in the data structure the frequencies, amplitudes and dwell times. As but an example where the user has selected a power conservation protocol and has selected to deliver signals to elicit two stimulation responses during each sweep, the processor would select and assign to two addresses at the data structure data corresponding to a frequency, amplitude and dwell time sufficient to elicit the desired stimulation response for the desired interval. For time intervals during the sweep between the stimulating parameters, the processor would select frequencies, amplitudes and dwell times to conserve power. During a sweep cycle the processor reads the data stored at the addresses in the data structure and generates signals corresponding thereto. These signals are provided to a frequency and amplitude generator which converts the processor signals into electric current of the corresponding amplitudes and frequencies for the designated dwell periods. Means such as electrodes are provided to deliver the electric current to the tissue to elicit the desired response. According to the preferred embodiment, the sweep data is stored sequentially at the data structure and during each sweep cycle sequentially retrieves the data from the addresses in order and supplies the data to the generator.

The frequency, amplitude and dwell periods for intervals between selected parameters may be randomly selected or preferably are selected to correspond to pre-determined sweep period wave-forms dictated by the predetermined protocols.

According to another embodiment the data structure may be embodied as a look-up table of addresses where at each address there is data corresponding to each of a frequency, dwell time and amplitude. Either in a pre-selected, random or pseudo-random fashion the addresses are selected and the data at each address is transformed into corresponding signals to be applied to the tissue.

Parameters may be programmed into a processor to select or screen the selection of the addresses to configure the sweep cycle so to, for example, conserve power, maximize the stimulation rate, provide for tissue heating without soliciting a stimulation response, e.g. muscle contraction or the like.

As can be appreciated by providing the data structure with hundreds or thousands of different frequency, dwell time and amplitude data each at a discrete address, the device is versatile. In one configuration, it may be programmed to select addresses to conserve power and thus make the device suitable for being powered by batteries. In another configuration the device can be programmed to select addresses to maximize the stimulation rate by "frequency hopping" by selecting those addresses whose frequencies are likely to elicit a stimulation response such as a muscle contraction of nerve reaction. In still another configuration the device can be programmed to select addresses completely at random or in a pseudo-random fashion to elicit a desired stimulation response while not conditioning the tissue not to react to the stimulus. In yet another configuration, the addresses may be selected to provide heating to the tissue without selecting an address having a frequency likely to elicit a stimulus response.

BRIEF DESCRIPTION OF THE DRAWINGS

These and other features and advantages will become better appreciated as the same becomes better understood with reference to the description wherein:

FIG. 3A is a chart showing stimulus frequency versus time for a device and method of the type according to the prior art where amplitude is held constant and frequency is swept between corner frequencies F8 and F1 for equivalent dwell times and showing the power delivered;

FIG. 3B is a graph showing for the example of FIG. 3A the total energy delivered during the sweep period;

FIG. 5A is a chart showing stimulus frequency versus time for a device and method of the type according to the present invention where amplitudes and frequencies are selected to deliver more energy without exceeding the stimulus threshold;

FIG. 5B is a graph showing for the example of FIG. 4A the total energy delivered during the sweep period;

DESCRIPTION

Figure 1:
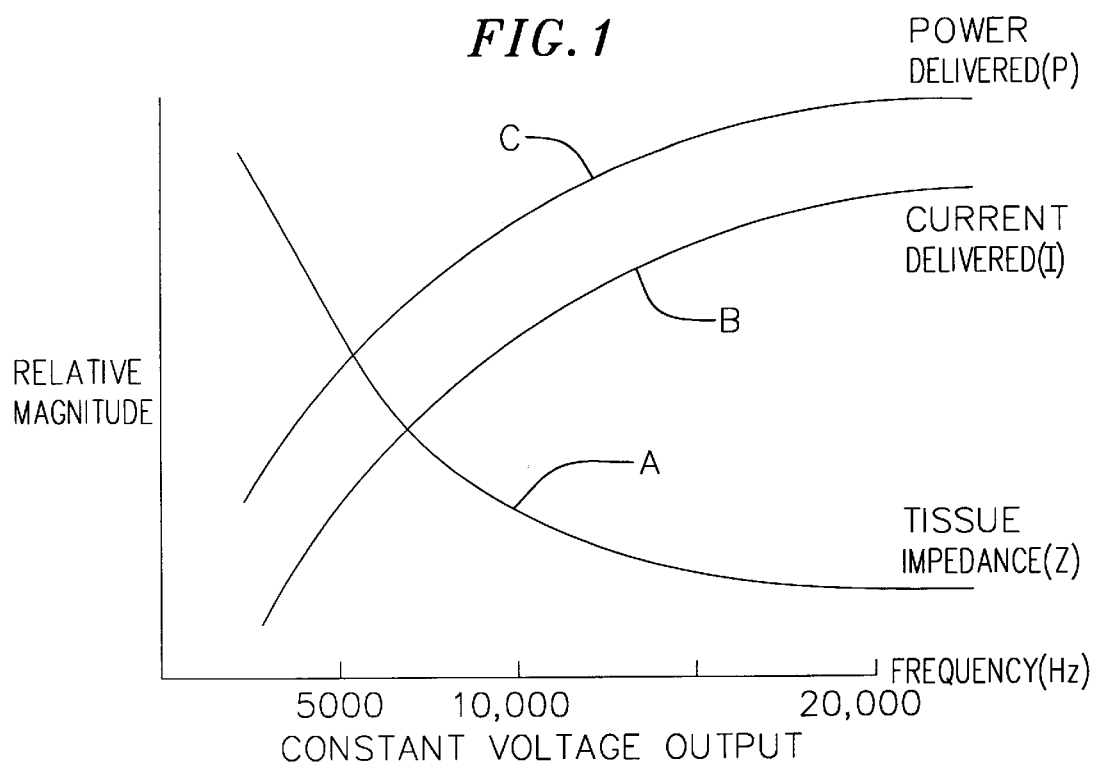
FIG. 1 is a graph showing the relationship between impedance, current and power versus frequency.
Figure 2:
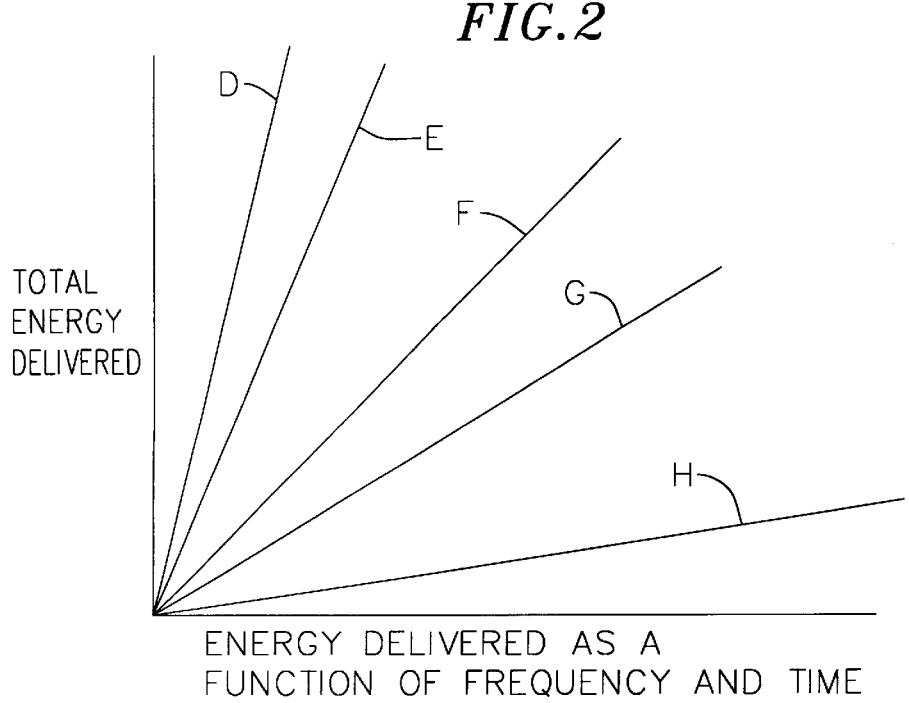
FIG. 2 is a graph showing the relationship of energy, frequency and time.

Turning to FIG. 3, there is shown a relative graph showing parameters for operation of a device according to the prior art device described in the above-identified '552 patent. With reference to FIG. 3, F8 and F1 represent the selected corner frequencies where frequency F8 is the upper frequency and F1 is the lower frequency. These corner frequencies may be, for example, 2000 Hz (F1) and 20,000 Hz (F8). Between the frequencies F1 through F8 the frequencies incrementally increase in a linear, ramping fashion during a sweep cycle from F8 to F1 and back to F8 as shown between the minimum and maximum frequencies F1, F8.

These prior devices operate by repetitive sweeping in a linear fashion up and down between the corner frequencies F1, F8 as suggested in FIG. 3. The sweeping is done in incremental steps wherein each frequency F1–F8 is maintained for equal and pre-selected dwell periods shown as DP1–DP16. Thus, looking at the right side of the graph of FIG. 3, the device would apply the high corner frequency F8 for a first dwell period DP1 and would then apply the second frequency F7 for the second, but equal, dwell period DP2 and so on as the frequencies are increased and decreased in the aforementioned and illustrated fashion. Each dwell period DP1–DP16 may be on the order of 1.0 msec.

These prior devices, during the sweeping, maintained the frequency amplitude as constant relying upon the changing frequencies to elicit the desired stimulation response.

With continuing reference to FIG. 3, there are shown vertical vectors SV1 through SV15 which are proportional to the amplitude (which is constant) and the frequency as shown by the stimulus threshold function:

$$Sv_n = c(\text{amplitude} \div \text{frequency}) \text{ where } c \text{ is a constant.}$$

Accordingly, in that frequency F8 is greater than the frequency F1, the vector SV1 is of a lesser magnitude than the frequency SV8 corresponding to frequency F1.

As can be appreciated, as the frequencies are swept through their individual dwell periods DP1–DP16 and the differential frequencies, the vectors SV1 increase at each dwell period to a maximum at a position corresponding to frequency F1 at dwell period DP8. At this point, the vector SV8 crosses a stimulus threshold value triggering a stimulus response of the cell, nerve or muscle. This threshold may be, for example 10,000 Hz at 70 mamp. This stimulus response may be a muscle contraction, "nerve blocking" to interrupt the sending of pain signals by the nerve or the like. As can be appreciated as the frequencies F1–F8 are swept back and forth an action potential is obtained when the stimulus threshold is crossed at the frequency F1 to elicit the desired response.

With continuing reference to FIG. 3, there is also shown associated with each dwell period DP1–DP15 the incremental power delivered for each dwell period DP1 through DP15. In that the dwell times DP1 through DP15 are constant and equal, the power delivered is shown by the darkened sections associated with each dwell period DP1–DP15. As can be appreciated because power, where amplitude and time are constant, is proportional to frequency, more power is consumed for the high corner frequency F8 than is for the low corner frequency F1.

At FIG. 3B a scale showing the total energy delivered to the subject area for the combined dwell period DP1 through DP15 of FIG. 3A. The energy is defined by the equation:

$$\Sigma^{DP1-15} Power \times Dwell\ Time$$

As can be appreciated according to the prior art technique illustrated in FIG. 3, the stimulus threshold is reached through the sweeping of the frequencies at constant amplitude and, by the structure and nature of the ramping and sweeping, the total energy delivered is fixed by the arrangement. There is no technique according to this system to minimize the energy delivered, so as to provide for battery operated devices, or to increase the power delivered to the site for heating without reaching the action potential and exceeding the stimulus threshold without, for example, increasing the frequencies F8 and F1, the corner frequencies, to a level exceeding the stimulus threshold which would result in the imposition of perhaps detrimental amounts of energy.

Figure 7:
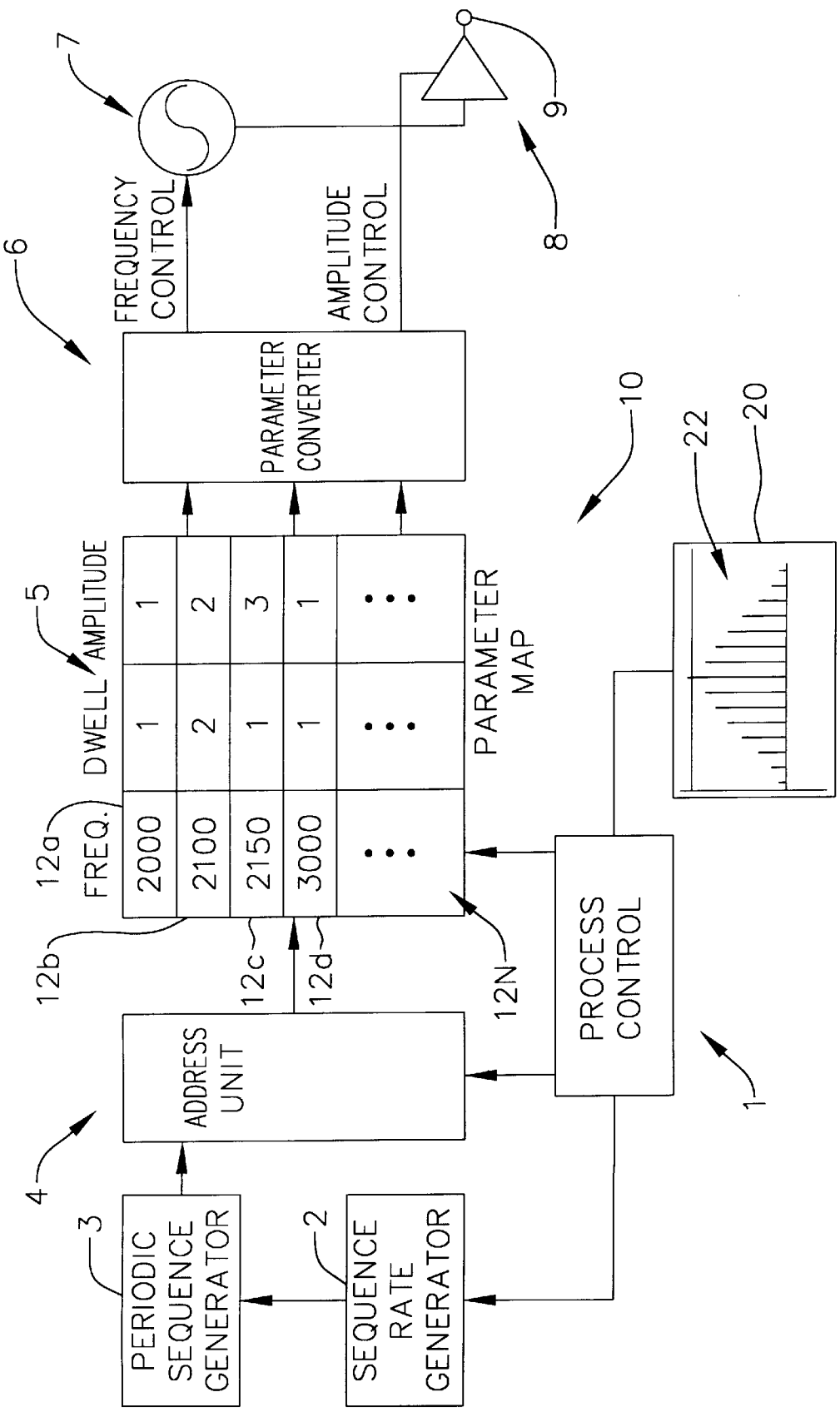
FIG. 7 is a diagram of the system according to the present invention.

Turning to FIG. 7, is a diagram of the device 10 according to the present invention. The device 10 includes a preprogrammed computer processor, shown as process control 1, which can be any suitable processor adapted for the purposes as hereinafter described.

Figures 4A, 4B:
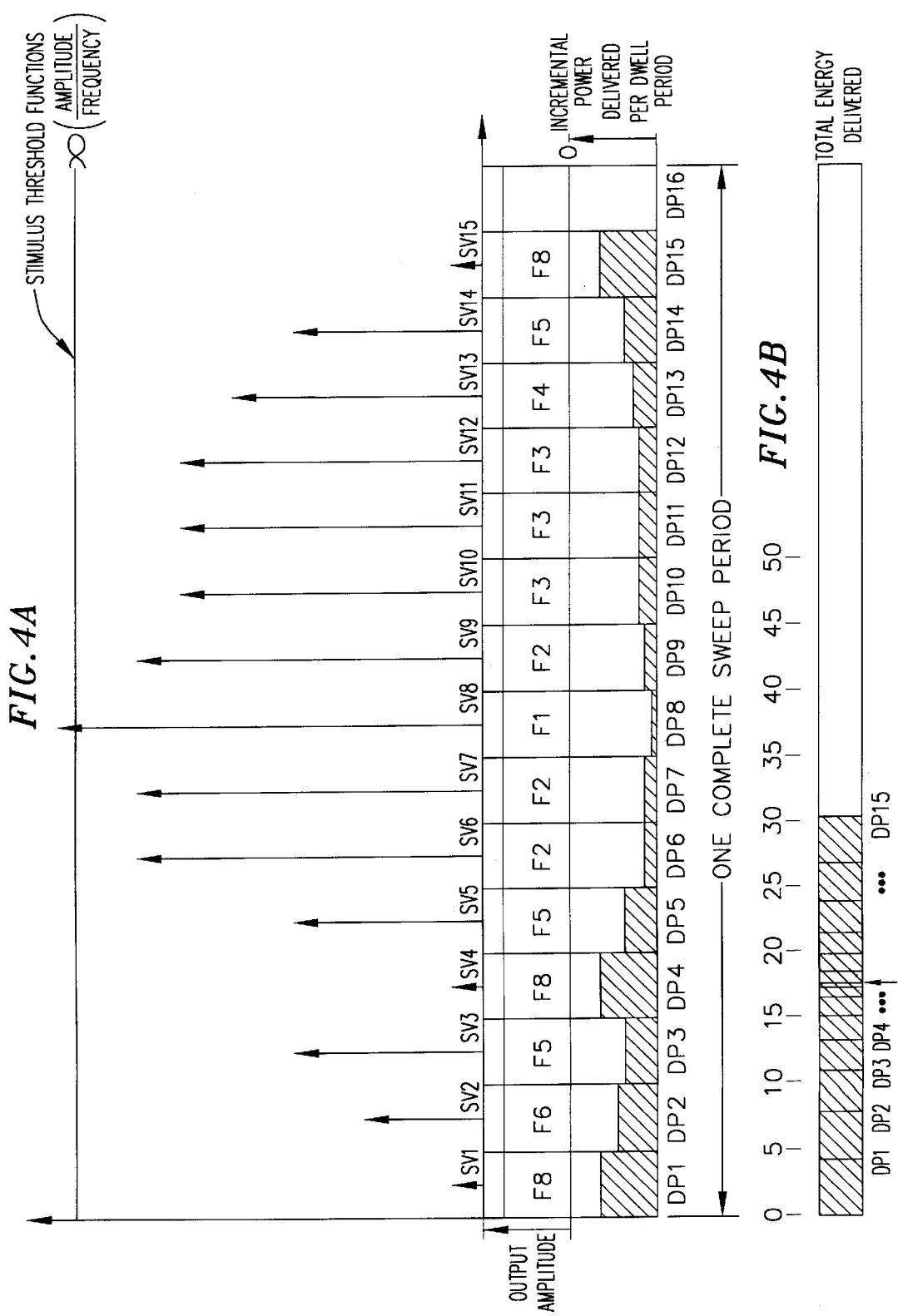
FIG. 4A is a chart showing stimulus frequency versus time for a device and method of the type according to the present invention where amplitude and dwell time is held constant and frequency is non-linearly changed to produce an action potential at the stimulus threshold while reducing the energy delivered.
FIG. 4B is a graph showing for the example of FIG. 4A the total energy delivered during the sweep period.

Means are provided by which the user of the device 10 may select various parameters and protocols to provide electro-therapeutic signals to tissue and/or nerves. These means preferably include a display 20 which is adapted to display the wave-form 22 for a selected sweep cycle and controlled by the control 1. By data input means such as touch screen technology for the display 20, a keyboard (not shown), mouse (not shown) or light pen (not shown) the user of the device 10 may select one or more parameters to be included in the sweep cycle. For example, the user may input into the control that he wishes to elicit during a sweep period a stimulation response of a muscle contraction while using reduced amounts of energy. This may be done by selecting an overall protocol of energy conservation and inputting the frequency and/or amplitude to elicit the desired response. As but an example the user would, through touch screen technology, select the energy conservation protocol whereupon the control 1 controls the display 20 to display a energy conservation protocol wave-form such as that shown as 22. The user then selects the parameters of one of frequency or amplitude at a location on the wave-from 22 to result in a vector SV8 having a function value sufficient to cross the stimulus threshold as shown in FIG. 4 to elicit the desired response. This function value may also be selected to elicit a nerve response such as blocking pain. Based upon the selected parameters of the energy conservation protocol and the vector SV8, the control 1 sends data corresponding to the selected dwell time, frequency and amplitude for each dwell period DP1–DP16 comprising the sweep cycle to a data structure 5 as shown in FIG. 7.

The data structure 5 includes a listing of the aforesaid data stored at discrete addresses $12a$–$12n$. At each address $12a$–$12n$ there is stored data corresponding to a frequency, dwell time and amplitude. As shown in FIG. 7 at address $12a$ there is represented data stored corresponding to a frequency of 2000 Hz, a dwell period scalar of 1 and an amplitude scalar of 1. It is to be understood that the data stored at the addresses $12a$–$12n$ can represent the actual frequency, dwell time period and amplitude or it can be scalars or multipliers of a fixed base frequency, dwell period or amplitude. Thus at each address $12a$–$12n$ there is stored data representing, for each dwell period during a sweep cycle, a frequency and amplitude to be applied. Thus as each address $12a$–$12n$ is accessed by the control 1, the stored data is used to construct the wave-form for the sweep cycle.

The processor controls a sequence rate generator 2 which controls the dwell time steps, DP1 through DP15 in FIG. 4 and which indirectly controls the sweep cycle rate between the parameters as herein described. It is to be understood that while only 15 dwell periods are shown for purposes of illustration, that more or less periods could be used to define the sweep cycle. The sequence rate generator 2 is programmed or controlled by the process control 1 to scale the data stored at the data structure 5 to increase or decrease the respective dwell times. That is, the sequence rate generator 2 can speed up or slow down the sweep rate cycle as defined by the data stored at the data structure 5. For example, if the stored data at address $12a$ is 1, that data is scaled by the sequence rate generator to be 1 msec, 0.1 msec, 0.001 msec or any other time period. As can be understood, since the sweep cycle rate is defined by the sum of the dwell periods constituting the sweep cycle, by scaling the data the sweep cycle rate, i.e. how long it takes to complete a sweep cycle, can be increased or decreased. As described herein, the device 10 is adapted to sequentially repeat the sweep cycle to provide the desired therapeutic effect.

The process control 1 also communicates with a periodic sequence generator 3 which is adapted to select either at random or in a predetermined, programmed fashion, the data to be stored at each address $12a$–$12n$. As set forth above, the selection of the data to be stored may be based upon the user's selection of an overall protocol and selection and the value of one or more individual vectors SV1–15. The data based upon the user's input is stored in a sequential fashion in the map defining the data structure 5. The periodic sequence generator 3 may randomly select data for those intervals in the sweep cycle not set by the user or can, as described above, select the "non-selected" parameters based upon the overall protocol.

Alternatively, the user may select to, for example, elicit two responses and the sequence generator 3 would select the data for those responses sufficient to elicit the responses and randomly position the locations of those vectors as well as for the intervening dwell periods to construct the sweep cycle wave-form.

In yet another embodiment, a second data structure may be provided (not shown in FIG. 7, which contains a listing of addresses and data for a universe of frequencies, dwell periods and amplitudes. The sequence generator 3 would select the addresses corresponding to the selected protocol and specific parameters to construct the desired sweep cycle wave-form and transfer the data to the data structure 5 to be accessed. For non-selected intervals in the wave-form the control 1 would select the addresses based upon the desired overall protocol, could randomly select addresses or could pseudo-randomly select addresses based upon certain parameters such as no amplitude or frequency data will be used if it could result in a vector value sufficient to create a stimulation response.

With continuing reference to FIG. 7, the control 1 is in communication with the address unit 4 and the data structure 5 to access the addressed data in the data structure 5.

Accordingly, under the control of the process control 1, sequence rate generator 2, periodic sequence generator 3 and address unit 4, addresses are selected and scaled in sequence. For example, and with reference to FIG. 7, the data for the sweep rate cycle wave-form is stored in sequence 12a–12n. As each address is selected by the address unit 4, the data representing the frequency, dwell time and amplitude for that map address is retrieved and issued to a parameter convertor 6 which, in turn controls, a medium frequency (MF) current generator 7 and an amplitude control output amplifier 8 to produce the frequency and amplitude of the corresponding address in the data structure 5 for the corresponding dwell time, as scaled by the sequence rate generator 2. These parameters are applied to the tissue through electrodes 9 to produce the desired effect. At the conclusion of the dwell time for the address 12a, the second address 12b is accessed, its parameters converted by the convertor 6 and those parameters are applied through the electrodes 9 to the tissue. In a similar fashion, as the address unit 4 sequentially accesses the addresses 12a–12n the wave-form of the sweep cycle is applied to the tissue to provide the desired therapeutic effects. At the conclusion of accessing the last address 12a–12n of the sweep cycle, the address unit 4 return to address 12 a and repeats the sweep cycle. Alternatively, the sweep cycle could be controlled to represent the data read in reverse order, i.e. 12n–12a. Thus the repetitions of the sweep cycle could be based upon repetitively reading the data in ascending order (12a–12n), or in ascending and descending order (12a–12n, 12n–12a, 12a–12n . . . ). The repetitions of the sweep cycle continue until a preprogrammed time period has elapsed or the device 10 is turned off.

Figure 6:
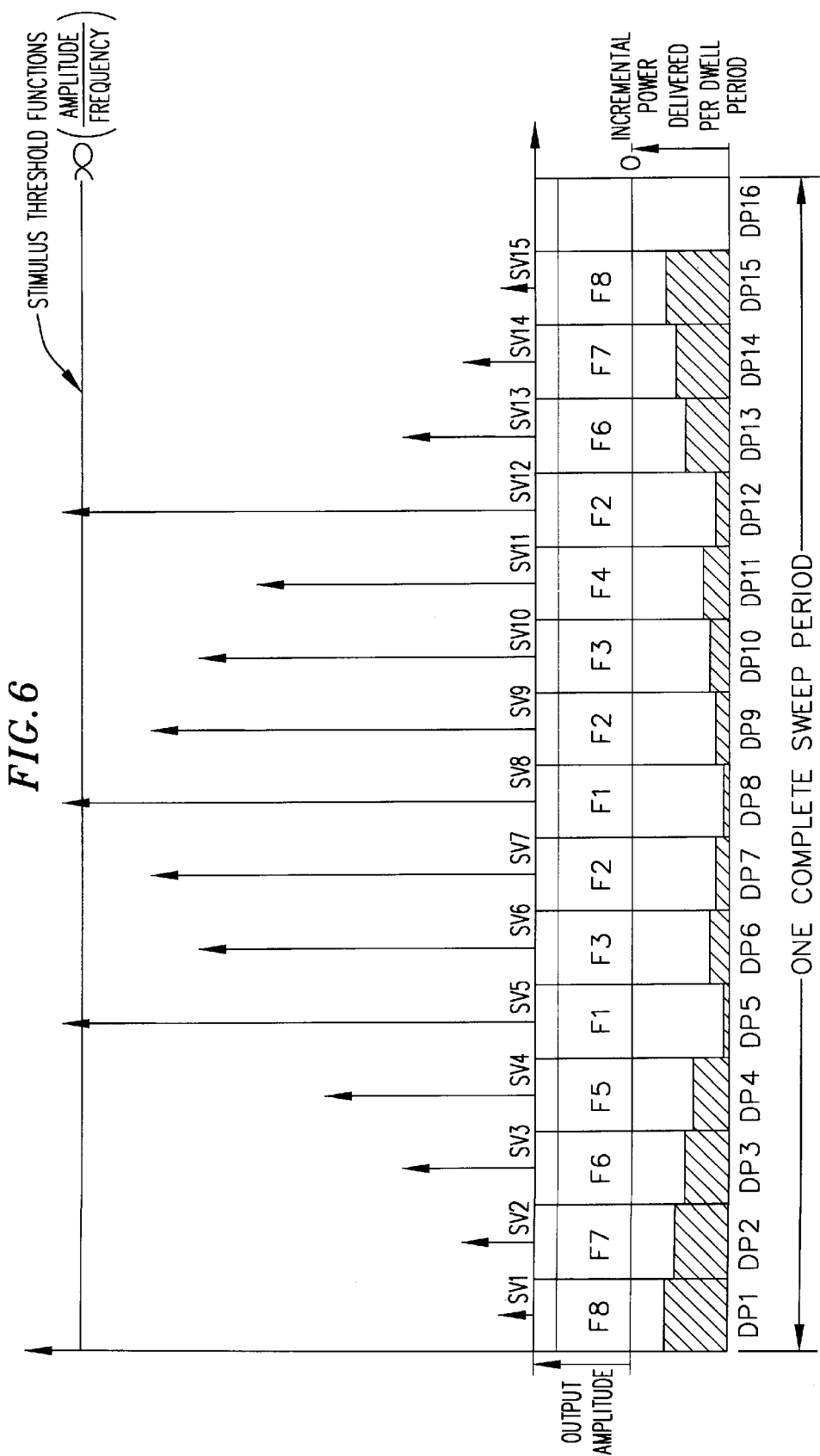
FIG. 6 is a chart showing stimulus frequency versus time for a device and method of the type according to the present invention optimized to produce three action potentials during a sweep period.

With reference to FIGS. 4 through 6 the device 10 can be used to generate various desired sweep cycle wave-forms. In FIG. 4 there is seen a wave-form which is constructed to elicit an action potential at vector SV8 and at the same time conserve energy. In comparison to the wave-form of prior devices shown in FIG. 3, the frequency "hopping" effect of the wave-form conserves energy, imposes vector values SV1–SV15 which do not permit the tissue, e.g. muscle, to become conditioned to anticipate the action potential. As shown, the vectors SV1 through SV15 are not ramped but instead are derived by the parameters at each address 12a–12n selected. Based upon the selection of the data the sweep cycle shown in FIG. 4 not only produces an action potential at F1 where the stimulus threshold is exceeded but also required less energy than the ramping system illustrated in FIG. 3. By the frequency hopping, energy and power can be conserved while still obtaining the same effect.

Turning to FIG. 5, there is seen a graph similar to that of FIG. 3 and FIG. 4 where the program sequence under control of the process control 1 and the other components described above selects data for the data structure 5 which not only varies the frequency but does so in a matter so as not to exceed the stimulus threshold (and elicit an action potential) at the same time maximizing the total energy delivered to the tissue to provide for heating thereof. This wave-form shown as a straight line does not produce a vector SV1–SV15 which exceeds the action potential to produce a response such as a muscle contraction.

Turning to FIG. 6, there is a graph shown similar to that of FIGS. 3–5 showing a sweep cycle selected to produce three action potentials during one sweep cycle simply by selecting the proper parameters (frequency and/or amplitude) for vectors SV5, SV8 and SV12 and loading the corresponding data into the data structure 5. It should be noted that the value of the action potential values varies depending upon the individual being treated, tissue density and the like. The intervening intervals of SV1–SV4, SV5–SV6, SV9–SV11 and SV13–SV15 for the sweep cycle may be randomly selected or selected to conserve power, provide heating or the like. As can be appreciated, the wave-form of FIG. 6 is not a linear, ramping form but instead hops to the action potential in a non-linear fashion thereby avoiding anticipation of the action potential which would occur with a ramped wave-form.

Figure 8:
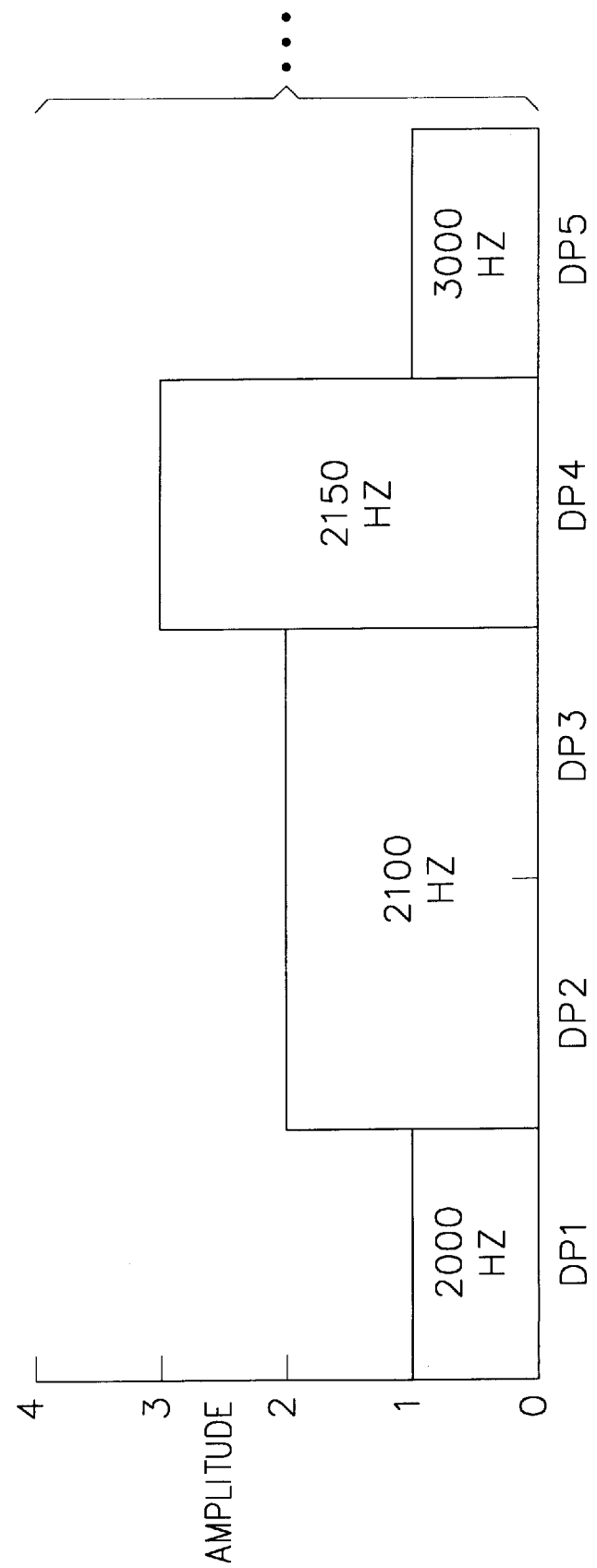
FIG. 8 is a graph illustrating the amplitudes and frequencies selected.

Finally, turning to FIG. 8, there is shown a graph illustrating the amplitudes and frequencies selected for the data structure 5 addresses 12a–d. For the dwell period DP1 at address 12a, which is of a single magnitude, there is applied a 2000 HZ frequency, for the second address 12b, there is applied a frequency of 2100 HZ for two dwell periods (DP2–DP3) at an amplitude magnitude of 2. The remaining data for addresses 12c–12d are shown in FIG. 8.

By the ability to randomly hop through vector magnitudes, the device 10 and the method provided by the device can be infinitely variable to produce multiple action potentials and stimulus responses during any sweep through the program, not to produce an action potential, to reduce energy consumed by the system or for any other desired effect. Further since ramping is not required, the tissue such as muscle cannot anticipate the occurrence of an action potential by the gradual, linear increasing of the vector magnitudes. This results in less energy consumption and more efficient delivery of energy in that, should the tissue become conditioned, the magnitude of the vector will have to be increased to produce the stimulation response.

While we have shown and described certain embodiments of the present invention, it is to be understood that it is subject to many modifications and changes without departing from the spirit and scope of the appended claims.

I claim:

1. A multi-parameter bio-electric device for electro-stimulation therapy comprising:

a data structure adapted to store at discrete addresses thereof combinations of frequency, dwell time and amplitude;

means for selecting a therapy protocol to be delivered over a sweep cycle;

means for selecting at least one of frequency or amplitude to be delivered during said sweep period;

a processor programmed to, in response to the selected parameters of therapy protocol and said one of frequency or amplitude to store in a data structure a listing of combinations of frequency, dwell time and amplitude to be delivered during a sweep cycle, said processor adapted to issue data signals corresponding to said combination listings for each sweep cycle;

a frequency and amplitude generator to receive the data signals and to output signals at frequencies, amplitudes and for the dwell time periods corresponding to said signals; and means for applying said output signals to tissue for electro-stimulation thereof.

2. The device of claim 1 including said processor programmed to store said data in the order of delivery, said processor for each cycle issuing data signals in said order.

3. The device of claim 2 including selecting the relative position during said sweep cycle where a selected one of said frequency or amplitude is to be delivered, said processor adapted to select and store the remaining data for the sweep cycle at the data structure corresponding to said protocol.

4. The device of claim 3 wherein said processor is adapted to randomly select said remaining data.

5. The device of claim 3 including means for selecting at least one action potential during said sweep cycle.

6. The device of claim 3 including means for selecting at least a plurality of action potentials.

7. The device of claim 1 further including a second data structure storing at discrete addresses in the second data structure data corresponding to combinations of dwell time, frequency and amplitude, said processor adapted to select said data from said second data structure corresponding to said parameter selecting means and said protocol selecting means.

8. A method for delivering electrical stimulation to tissue comprising:
   selecting an overall protocol for the stimulation to be delivered during a sweep period;
   selecting one of a frequency or amplitude to be delivered during the sweep period;
   providing a processor which, based upon said selected protocol and said one of frequency or amplitude, constructs at a data structure a listing of frequencies, amplitudes and dwell periods for the sweep cycle and issues signals corresponding to the listing; and
   generating electrical signals in response to the signals from the processor to the tissue at the frequency and amplitude and for the dwell period corresponding to said listing.

9. The method of claim 8 wherein the processor constructs a sequential listing and issues signals for each cycle corresponding to sequential retrieval of data from each listing.

10. The method of claim 8 including selecting several data of one of frequency or amplitude to be delivered at spaced intervals during the sweep cycle and said processor, based upon said selected protocol, selecting the data for said listing corresponding to the remaining time intervals during the cycle.

11. A multi-parameter bio-electric device for electro-stimulation therapy comprising:
   a data structure including data corresponding to varying combinations of frequency, dwell time and amplitude stored at discrete addresses in said data structure;
   means for selecting a sequence of a plurality of address data to define a periodic sequence and for scaling the dwell time data for each address;
   a frequency and amplitude generator adapted to receive the data from said selecting means and output of signals at frequencies, amplitudes and for dwell times dictated by said data of said selected periodic sequence; and
   means for applying said output signals to tissue for electro-stimulation thereof.

12. The device of claim 11 wherein said selecting means is adapted to randomly selecting said address sequence.

13. The device of claim 11 further including a processor pre-programmed with predetermined periodic sequences, said selecting means selecting said address sequence corresponding to said predetermined periodic sequence.

14. The device of claim 11 wherein said selecting means is adapted to select said addresses in a pseudo-random fashion.

15. The device of claim 14 including means for pre-selecting the parameters of said periodic sequence in terms of frequency or amplitude, said selecting means selecting said sequence of a plurality of addresses where the data for each selected address corresponds to said pre-selected parameters.

16. A multi-parameter bio-electric device for electro-stimulation therapy comprising:
   a processor;
   a data structure including a table of data corresponding to varying combinations of frequency, dwell time and amplitude stored at discrete addresses in said table in said data structure;
   a periodic sequence generator controlled by said processor to select a sequence of addresses in said table to define a periodic sequence of signal parameters of frequency, dwell time and amplitude;
   a sequence rate generator controlled by said processor to receive data corresponding to each address of said selected sequence and scale the dwell time data for each address;
   a frequency and amplitude generator controlled by said processor to receive the data from said sequence rate generator and output of signals at frequencies, amplitudes and for dwell times dictated by said data of said selected periodic sequence scaled by said sequence rate generator; and
   means for applying said output signals to tissue for electro-stimulation thereof.

17. The device of claim 16 including means for randomly selecting the addresses for said periodic sequence.

18. The device of claim 17 wherein said random selection means includes said processor having a random number generator and each address for the table has an assigned number, said periodic sequence generator controlled by said processor and random number generator select said addresses in a random fashion.

19. The device of claim 16 wherein said processor includes means for selecting for the periodic sequence parameters of at least one of said frequency or amplitude and for controlling said periodic sequence generator to, in selecting said periodic sequence, exclude addresses wherein the data contained therein does not correspond to said selected parameters.

20. The device of claim 19 including means to randomly select addresses for said periodic sequence.

21. A multi-parameter bio-electric device for electro-stimulation therapy comprising:
   a processor including a first data structure storing address data corresponding to at least one pre-selected periodic sequence of signals for electro-stimulation, a random number generator, means for selecting between said pre-selected periodic sequence and a randomly selected periodic sequence and means for entering parameter data to select a limit for one of said frequency or amplitude of said electro-stimulation signals;
   a second data structure including a table of data corresponding to varying combinations of frequency, dwell time and amplitude stored at discrete, numbered addresses in said table in said data structure;
   a periodic sequence generator controlled by said processor to (i) select a sequence of table addresses including data corresponding to said pre-selected periodic sequence, (ii) to randomly select by said random number generator a plurality of table addresses of data for said periodic sequence, or (iii) select table addresses of data corresponding to said parameter data for said periodic sequence;

a sequence rate generator controlled by said processor to receive data corresponding to each address of said selected sequence and scale the dwell time data for each address;

a frequency and amplitude generator controlled by said processor to receive the data from said sequence rate generator and output of signals at frequencies, amplitudes and for dwell times dictated by said data of said selected periodic sequence scaled by said sequence rate generator; and means for applying said output signals to tissue for electro-stimulation thereof.

\* \* \* \* \*